United States Patent [19]

Stanek

[11] 4,273,766
[45] Jun. 16, 1981

[54] NITROSO-UREA DERIVATIVES

[75] Inventor: Jaroslav Stanek, Birsfelden, Switzerland

[73] Assignee: Ciba-Geigy Corporation, Ardsley, N.Y.

[21] Appl. No.: 29,495

[22] Filed: Apr. 12, 1979

Related U.S. Application Data

[63] Continuation-in-part of Ser. No. 913,776, Jun. 8, 1978, abandoned, and a continuation-in-part of Ser. No. 14,195, Feb. 22, 1979, abandoned.

[30] Foreign Application Priority Data

Jun. 15, 1977 [CH] Switzerland ............... 7359/77

[51] Int. Cl.³ .................. A61K 31/70; C07H 15/04
[52] U.S. Cl. ............................... 424/180; 536/4; 536/18; 536/53; 536/54; 536/55
[58] Field of Search ............ 536/4, 18, 22, 53, 54; 424/180

[56] References Cited

U.S. PATENT DOCUMENTS

| | | | |
|---|---|---|---|
| 3,940,383 | 2/1976 | Fajwara et al. | 536/4 |
| 4,057,684 | 11/1977 | Kimura et al. | 536/53 |
| 4,086,415 | 4/1978 | Suami et al. | 536/4 |

OTHER PUBLICATIONS

Machinami, T. et al., Bull. Chem. Soc. Japan, 48, 1975 (3761-3762).

Machinami, T. et al., Bull. Chem. Soc. Japan, 46, 1973 (1013-1014).

MOntero, J., et al., C. R. Acad. Sc. Paris, 277, 809-C, 1974.

Bannister, B., J. Antibiotics, 25, 1972 (377-386).

*Primary Examiner*—Johnnie R. Brown
*Assistant Examiner*—Blondel Hazel
*Attorney, Agent, or Firm*—Prabodh I. Almaula

[57] ABSTRACT

The present invention relates to new nitroso-urea derivatives, particularly to $N_1$-glucofuranosid-6-yl-$N_3$-nitroso-ureas, of the general formula I

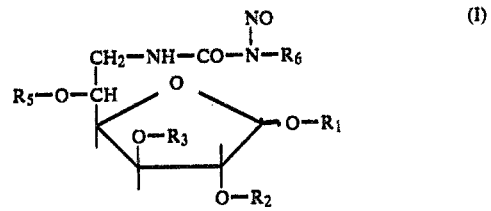

wherein anyone of $R_1$, $R_2$, $R_3$ and $R_5$ represent hydrogen, optionally substituted alkyl, aralkyl or acyl, or $R_1$ and $R_2$ together or $R_3$ and $R_5$ together also represent alkylidene or cycloalkylidene, and $R_6$ represents optionally substituted alkyl; and to processes for producing them.

14 Claims, No Drawings

NITROSO-UREA DERIVATIVES

CROSS-REFERENCE

This is a continuation-in-part application to U.S. applications Ser. No. 913,776 filed June 8, 1978 now abandoned and No. 014,195 filed Feb. 22, 1979 now abandoned.

This invention relates to new nitroso-urea derivatives, particularly to $N_1$-glucofuranosid-6-yl-$N_3$-nitroso-ureas, of the general formula I

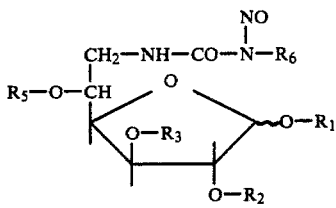

wherein anyone of $R_1$, $R_2$, $R_3$ and $R_5$ represent hydrogen, optionally substituted alkyl, aralkyl or acyl, or $R_1$ and $R_2$ together or $R_3$ and $R_5$ together also represent alkylidene or cycloalkylidene, and $R_6$ represents optionally substituted alkyl.

Except where otherwise stated in the following, groups, radicals or compounds modified by the term "lower" preferably contain up to 7, particularly up to 4, carbon atoms.

The new compounds have a very good action in the case of several different forms of transplantable tumours and leukaemia, and also to some extent in the case of virus-induced leukaemia.

Alkyl is in particular lower alkyl, for example isopropyl, straight-chain or branched-chain butyl, pentyl, hexyl or heptyl, and especially methyl, ethyl or n-propyl, in each case bonded in any position.

Suitable substituents of the optionally substituted alkyl group are in particular free or etherified hydroxyl groups, for example lower alkoxy groups, or halogen atoms. Here the substituted alkyl group, such as the lower alkyl group, can carry one, two or more identical or different substituents, especially free hydroxyl groups or halogen atoms.

Aralkyl is above all aryl-lower-alkyl, the lower alkyl moiety corresponding in particular to the aforementioned lower alkyl, being especially methyl or ethyl. The aromatic moiety is particularly a monocyclic, as well as bicyclic, aryl group, especially phenyl, also however naphthyl. It can be optionally mono-, di- or polysubstituted for example by lower alkyl groups, by free or etherified hydroxyl, for example lower alkoxy or lower alkylenedioxy, or by halogen atoms and/or trifluoromethyl. To be particularly mentioned are 2-phenylethyl, chlorobenzyl, methylbenzyl, hydroxybenzyl, methoxybenzyl, or especially benzyl.

The alkylidene group is in particular a lower alkylidene group, such as the 2-butylidene, 3-pentylidene and above all isopropylidene group.

The cycloalkylidene group contains preferably 5-7ring carbon atoms and is, in particular, cyclopentylidene or cyclohexylidene.

Acyl is especially an acyl group of an organic acid, particularly of an organic carboxylic acid. Thus acyl is above all alkanoyl, having in particular 2-18 carbon atoms, such as acetyl or propionyl, or aroyl, such as naphthoyl-1, naphthoyl-2 and especially benzoyl, or benzoyl or naphthoyl substituted by halogen, lower alkyl, lower alkoxy, trifluoromethyl, hydroxyl or lower alkanoyloxy. Acyl can also be an acyl group of an organic sulphonic acid, for example of an alkanesulphonic acid, particularly a lower alkanesulphonic acid, such as methanesulphonic acid or ethanesulphonic acid, or of an arylsulphonic acid, especially of a phenylsulphonic acid optionally substituted by lower alkyl, such as benzenesulphonic acid or p-toluenesulphonic acid; and it can also be the radical of a carbamic acid, such as unsubstituted carbamoyl, lower alkylcarbamoyl or arylcarbamoyl, such as methylcarbamoyl or phenylcarbamoyl.

Lower alkyl as substituent of the above-mentioned radicals is in particular methyl or ethyl, and also n-propyl, isopropyl or straight-chain or branched-chain butyl.

Lower alkoxy as substituent of the above-mentioned radicals is above all methoxy or ethoxy, also n-propoxy, isopropoxy, n-butoxy or isobutoxy.

Halogen is for example fluorine, chlorine or bromine.

The new compounds can be in the form of anomeric mixtures or in the form of pure α- or β-anomers.

The new compounds have valuable pharmacological properties; they have in particular a very good action in the case of several different forms of transplantable tumours and leukaemia, and also to some extent in the case of virus-induced leukaemia. In intraperitoneal doses of 25–500 mg/kg they greatly inhibit the growth of tumours in mice with, for example, Ehrlich's ascitic carcinoma, or solid Harding-Passey's melanoma, and in rats with for example Yoshida's ascitic sarcoma. Analogous doses effect a prolongation of the life of mice, compared with the life of control mice with for example leukaemia L 1210 or Rauscher's leukaemia.

There ist thus effected with for example ethyl-6-desoxy-3,5-di-O-methyl-6-(3-methyl-3-nitrosoureido)-β-D-glucofuranoside in intraperitoneal doses of 50–250 mg/kg an 80–100% inhibition of the growth of the stated tumours, and in the case of leukaemia L 1210 a prolongation of life of about 60%; and after peroral administration to mice with Rauscher's leucaemia a prolongation of life of about 150%. With ethyl-6-desoxy-5-O-methyl-6-(3-methyl-3-nitrosoureido)-α-D-glucofuranoside at the same dosis in the case of leukaemia L 1210 the prolongation of life is of more than 90%. Compatibility is good. No secondary effects are observed even after prolonged treatment. In the case also of normal animals after peroral treatment for three weeks, no changes in organs are to be observed macroscopically.

The invention relates in particular to compounds of the formula I wherein $R_1$ and $R_2$ each represent hydrogen, lower alkyl optionally substituted by hydroxyl, lower alkoxy or halogen, or benzyl optionally sutstituted, particularly in the para-position, by hydroxyl, lower alkoxy, halogen or trifluoromethyl, or $R_1$ and $R_2$ together also represent lower alkylidene or cycloalkylidene having 5–6 carbon atoms, $R_3$ and $R_5$ each represent hydrogen, lower alkyl optionally substituted by hydroxyl, lower alkoxy or halogen, benzyl optionally substituted, particularly in the p-position, by hydroxyl, lower alkoxy, halogen or trifluormethyl, lower alkanoyl, for example acetyl or propionyl, or benzoyl optionally substituted by halogen, lower alkoxy, hydroxyl or lower alkanoyloxy, for example p-chlorobenzoyl, p-bromobenzoyl, p-methoxybenzoyl or o- or p-hydroxybenzoyl, or $R_3$ and $R_5$ together also represent lower alkylidene or cycloalkylidene having 5-6 carbon atoms, and $R_6$ represents lower alkyl optionally substituted by halogen, hydroxyl or lower alkoxy.

Particularly valuable compounds are those in which $R_3$ and $R_5$ represent an identical radical, or wherein $R_3$ is hydrogen and $R_5$ is lower alkyl.

To be particularly emphasised are compounds of the given formula I wherein $R_1$ represents lower alkyl, and $R_2$ represents hydrogen, or $R_1$ and $R_2$ together represent lower alkylidene, $R_3$ and $R_5$ each represent hydrogen, lower alkyl, or benzyl optionally substituted, especially in the p-position, by halogen, hydroxyl, lower alkoxy or alkyl, or $R_6$ represents lower alkyl optionally substituted by chlorine, for example methyl or chloroethyl.

Compounds of the formula I to be mentioned above all are those wherein $R_3$ represents hydrogen or methyl, $R_5$ represents methyl, $R_6$ represents methyl or chlorethyl, and $R_1$ represents hydrogen, methyl, ethyl or propyl, and $R_2$ represents hydrogen, or $R_1$ and $R_2$ together represent the isopropylidene group.

The new compounds are obtained by introducing, in a manner known per se, the nitroso group into a compound of the formula II

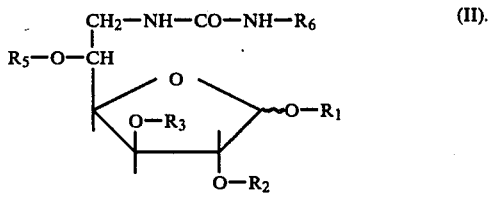

For this purpose, the compound of the formula II is preferably reacted with nitrous acid, or with salts or derivatives thereof. There is preferably used a salt, such as an alkali metal salt or alkaline-earth metal salt, particularly the sodium salt, of nitrous acid, and the nitrous acid is liberated from this with an acid, such as a mineral acid, e.g. hydrochloric acid, sulphuric acid or nitric acid, or with an organic acid, such as carbonic acid or acetic acid, or with a sulphonic acid, e.g. a lower alkanesulphonic acid such as methane- or ethanesulphonic acid, or with an ion exchanger containing sulphonic acid groups, e.g. Amberlite IR 120. It is also possible to use however an anhydride of nitrous acid, especially a mixed anhydride with, for example, nitric acid or a hydrohalic acid.

The reaction is performed if necessary in the presence of a solvent, and as solvent there can be used for example also an organic acid which is present. The reaction is preferably performed at low temperature, for example at $-10°$ to $30°$ C.

The starting materials used for this process are new. They can be obtained in a manner known per se from a corresponding glucofuranose unsubstituted in the 6-position, for example by reaction to a reactive ester, for example with an alkanesulphonic acid, arylsulphonic acid or hydrohalic acid, then to an azide, and reduction of the resulting azide to 6-desoxy-6-amino-glucofuranose, which is subsequently condensed with a suitable N-$R_6$-carbamic acid derivative, such as with a corresponding isocyanate to 6-desoxy-6-(3-$R_6$-ureido)-glucofuranose. As mentioned above, these reactions are performed in a manner known per se.

A further method for producing the new nitrosoureas comprises reacting a compound of the formula III

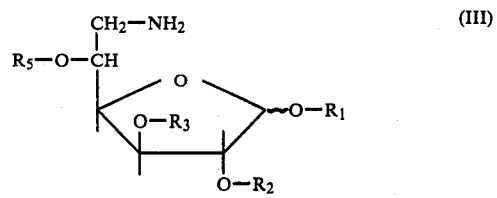

with a reactive derivative of an

N-nitroso-N-$R_6$-carbamic acid (IV)

The reactive derivative can be for example an acid anhydride, preferably a mixed acid anhydride, such as an acid azide or an activated ester. Activated esters which may be mentioned are in particular cyanomethyl esters, carboxymethyl esters, paranitrophenylthio esters, paranitrophenyl esters, 2,4,5-trichlorophenyl esters, pentachlorophenyl esters, N-hydroxy-succinimide esters, N-hydroxyphalimide esters, 8-hydroxyquinoline esters or N-hydroxypiperidine esters.

This reaction is performed in a manner known per se, preferably in a solvent such as water, in a halogenated hydrocarbon, e.g. dichloro- or trichloroethane, in an ether such as diethyl ether, tetrahydrofuran, dimethylformamide, dimethylsulphoxide, or in an optionally alkylated pyridine, such as pyridine, picoline, lutidine or quinoline.

The employed starting materials are known, and can be produced in a manner known per se. Thus, the amine of the formula III can be obtained from a corresponding glucofuranose unsubstituted in the 6-position, for example by reaction to a reactive ester, e.g. with an alkane- or arylsulphonic acid or with a hydrohalic acid, and then to an azide, and reduction of the azide thus obtained to give 6-desoxy-6-amino-glucofuranose.

The processes described in the foregoing are performed, by methods known per se, in the absence, or preferably in the presence, of diluting agents or solvents, if necessary with cooling or heating, under elevated pressure and/or in an inert atmosphere, e.g. in a nitrogen atmosphere.

The new compounds can exist as pure $\alpha$- or $\beta$-anomers or as anomeric mixtures. By virtue of the physical-chemical differences in the constituents, the last-mentioned can be separated in a known manner into the two pure anomers, for example by means of chromatographical separation, such as by thin-layer chromatography or by some other suitable separating method. Preferably, the more active of the two anomers is isolated.

The invention relates also to those process embodiments wherein a starting material is formed under the reaction conditions, or is used in the form of a reactive derivative or salt. There are preferably used starting materials which yield according to the processes of the invention the compounds described in the foregoing as being particularly valuable.

The present invention relates likewise to pharmaceutical preparations containing compounds of the formula I. In the case of the pharmaceutical preparations according to the invention, they are preparations which are suitable for enteral administration, such as oral and rectal administration, and also parenteral administration to warm-blooded animals, and which contain the pharmacological active substance either alone or together with a pharmaceutically applicable carrier material. The dosage of active substance depends on the species of warm-blooded animal, on the age and on the individual condition, as well as on the mode of administration.

The new pharmaceutical preparations contain from about 10% to about 95%, preferably from about 20% to about 90%, of active substance. Pharmaceutical preparations according to the invention can be in the form of, e.g., dosage units such as dragees, tablets, capsules, suppositories or ampoules. The pharmaceutical preparations of the present invention are produced in a manner known per se, for example by means of conventional mixing, granulating, coating, solution or lyophilising processes.

Suitable carriers are in particular fillers, such as sugar, e.g. lactose, saccharose, mannitol or sorbitol, cellulose preparations and/or calcium phosphates, e.g. tricalcium phosphate or calcium hydrogen phosphate, also binders such as starch paste, with the use for example of maize starch, wheat starch, rice starch or potato starch, gelatine, tragacanth, methyl cellulose, hydroxypropylmethyl cellulose, sodium carboxy methyl cellulose and/or polyvinylpyrrolidone, and/or, if required, effervescent agents, such as the above-mentioned starches, also carboxymethyl starch, cross-linked polyvinylpyrrolidone, agar, alginic acid or a salt thereof, such as sodium alginate. Auxiliaries are primarily flow-regulating agents and lubricants, e.g. silicic acid, talcum, stearic acid or salts thereof, such as magnesium stearate or calcium stearate, and/or polyethylene glycol. Dragee cores are provided with suitable coatings which are optionally resistant to gastric juices; for this purpose there are used, inter alia, concentrated sugar solutions optionally containing gum arabic, talcum, polyvinylpyrrolidone, polyethylene glycol and/or titanium dioxide, lacquer solutions in suitable organic solvents or solvent mixtures or, for the production of coatings resistant to gastric juices, solutions of suitable cellulose preparations, such as acetylcellulose phthalate or hydroxypropylmethylcellulose phthalate. Dyes or pigments can be added to the tablets or dragée coatings, e.g. for identification or for indication of the various doses of active substances.

The following Examples illustrate the invention described in the foregoing; they are however in no way intended to limit the scope of the invention. The temperature values are given in degrees Centigrade.

EXAMPLE 1

A solution of 15.8 g of sodium nitrite in 80 ml of water is added dropwise within 15 minutes to a solution, cooled to 0° C. of 60.7 g of ethyl-3,5-di-O-methyl-6-deoxy-6-(3-methylureido)-α-D-glucofuranoside in 500 ml of water and 15 ml of glacial acetic acid; the mixture is stirred for one hour at the same temperature, and allowed to stand for 16 hours at room temperature. The product which has crystallised out is filtered off with suction, washed with a small amount of ice water and dried. The mother liquor is extracted with chloroform, the organic phase is dried over magnesium sulphate, and the solvent is distilled off. The residue is purified by column chromatography on silica gel with methylene chloride/ethyl acetate (85:15); the crystalline product is combined with the first crystals obtained, and the whole is recrystallised from ether/petroleum ether. The resulting ethyl-3,5-di-O-methyl-6-deoxy-6-(3-methyl-3-nitrosoureido)-α-D-glucofuranoside melts at 90° C.; $R_f$ value 0.45 on silica gel thin-layer plates in the system methylene chloride/methanol (15:1); $[\alpha]_D^{20} = +43° \pm 1°$ (chloroform, c=1,465).

The starting material can be produced as follows: 67 ml of methanesulphonic acid chloride is added dropwise within 45 minutes, with stirring and external cooling, to a solution of 207 g of 3,5-di-O-methyl-1,2-O-isopropylidene-α-D-glucofuranose in 600 ml of absolute pyridine, and the mixture is allowed to stand for 4 hours at room temperature. An addition of 50 ml of water is made and, after a further 15 minutes, the major part of the pyridine is evaporated off. The residue is taken up in ether; the ethereal solution is washed with water, ice-cold 2 N hydrochloric acid, water, a saturated sodium hydrogen carbonate solution and water; and dried over magnesium sulphate, and the solvent is distilled off. The oily residue is 3,5-di-O-methyl-1,2-O-isopropylidene-6-O-mesyl-α-D-glucofuranose; $R_f$ value 0.35 on silica gel thin-layer plates in the system methylene chloride/acetic acid (85:15).

240 g of this product is dissolved in 1700 ml of N,N-dimethylformamide; there are added 142 g of sodium azide and 170 ml of water, and stirring is maintained at 110° C. for 3 hours. The reaction mixture is cooled and filtered, and the filtrate is concentrated by evaporation. The residue is taken up in ether, the solution is washed with water and dried over magnesium sulphate, and the solvent is distilled off to thus yield 6-azido-6-deoxy-3,5-di-O-methyl-1,2-O-isopropylidene-α-D-glucofuranose in the form of yellowish oil having an $R_f$ value of 0.61 on silica gel thin-layer plates in the system methylene chloride/ethyl acetate (85:15), and the optical rotation $[\alpha]_D^{20} = -57° \pm 1°$ (chloroform, c=1.915).

A solution of 193 g of this compound in 3500 ml of 1 N alcoholic hydrochloric acid is left to stand for 18 hours at room temperature. The major part of the solvent is then evaporated off in a water-jet vacuum; the residue is taken up in ether, and this solution is washed with water, with a saturated sodium hydrogen carbonate solution and again with water, dried over magnesium sulphate, and evaporated to dryness. The anomeric mixture obtained is separated by column chromatography on silica gel with methylene chloride/ethyl acetate (85:15). The resulting ethyl-6-azido-6-deoxy-3,5-di-O-methyl-α-D-glucofuranoside has the $R_f$ value of 0.32 on silica gel thin-layer plates in the system methylene chloride/ethyl acetate (85:15), and the optical rotation $[\alpha]_D^{20} = +56° \pm 1°$ (chloroform, c=0.89). The corresponding β-glucofuranoside gives in the same system the $R_f$ value of 0.11.

21.9 g of ethyl-6-azido-6-deoxy-3,5-di-O-methyl-α-D-glucofuranoside in 200 ml of ethanol is reduced, in the presence of 2 g of 5% palladium/charcoal, with hydrogen.

The catalyst is filtered off, and the alcohol is distilled off to leave ethyl-6-amino-6-deoxy-3,5-di-O-methyl-α-D-glucofuranoside in the form of yellowish oil.

To a solution of 74.9 g of this oil in 550 ml of ethanol is added dropwise, in the course of one hour, a solution of 18.5 ml of methylisocyanate in 60 ml of methylene chloride, and the reaction mixture is evaporated to dryness. The resulting ethyl-6-deoxy-3,5-di-O-methyl-6-(3-methyl-ureido)-α-D-glucofuranoside is crystallised from ethyl acetate/ether; m.p. 144°, $[\alpha]_D^{20} = +57° \pm 1°$ (chloroform, c=1.134) and $R_f$ value=0.22 on silica gel in the system methylene chloride/methanol (15:1).

EXAMPLE 2

A solution of 8.5 g of sodium nitrite in 40 ml of water is added dropwise within 30 minutes to a solution, cooled to 0°–5°, of 33.4 g of 3,5-di-O-methyl-6-deoxy-1,2-O-isopropylidene-6-(3-methylureido)-α-D-glucofuranose in 280 ml of water and 8.0 ml of glacial acetic acid. Stirring is maintained for one hour at 0°–5° and for 18 hours at room temperature. The solution is subsequently extracted with chloroform; the organic phase is washed with water, dried over magnesium sulphate, and evaporated to dryness. The residue is chromatographed on 1200 g of silica gel with methylene chloride/ethyl acetate (85:15). The fractions with the $R_f$ value of 0.41 containing 6-deoxy-3,5-di-O-methyl-1,2-O-isopropylidene-6-(3-methyl-3-nitrosoureido)-α-D-glucofuranose are concentrated to dryness; $[\alpha]_D^{20} = -49° \pm 1°$ (chloroform, c=1.127).

The starting material used can be produced as follows:

60.0 g of 6-azido-6-deoxy-3,5-di-O-methyl-1,2-O-isopropylidene-α-D-glucofuranose is dissolved in 600 ml of ethanol, and reduced, in the presence of 5% palladium/charcoal, with hydrogen. The catalyst is separated, and the solvent is distilled off to leave 6-amino-6-deoxy-3,5-di-O-methyl-1,2-O-isopropylidene-α-D-glucofuranose in the form of colourless oil. 33.2 g of this product is dissolved in 250 ml of ethanol, and to this solution is added dropwise in the course of 30 minutes, with stirring, a solution of 8.4 ml of methylisocyanate in 25 ml of methylene chloride. The reaction mixture is stirred for a further 60 minutes and then evaporated to dryness, and the residue is crystallised from acetone. The resulting 6-deoxy-3,5-di-O-methyl-1,2-O-isopropylidene-6-(3-methylureido)-α-D-glucofuranose having the $R_f$ value of 0.45 on silica gel in the system acetone, and $[\alpha]_D^{20} = -57° \pm 1°$ (chloroform, c=1.987), melts at 66°–69°.

EXAMPLE 3

A solution of 25.4 g of sodium nitrite in 130 ml of water is added dropwise within 45 minutes, with stirring, to a solution, cooled to 0°–5°, of 52.4 g of ethyl-6-deoxy-3,5-di-O-methyl-6-(3-methylureido)-β-D-glucofuranoside in 420 ml of water and 24.5 ml of glacial acetic acid; the mixture is stirred for 18 hours at the same internal temperature, and is subsequently extracted with chloroform; the organic phase is washed with water, dried over magnesium sulphate and evaporated to dryness. The residue is chromatographed on silica gel with methylene chloride/ethyl acetate (85:15). The fractions containing ethyl-6-deoxy-3,5-di-O-methyl-6-(3-methyl-3-nitrosoureido)-β-D-glucofuranoside with the $R_f$ value of 0.15 are combined, and evaporated to dryness: $[\alpha]_D^{20} = -57° \pm 1°$ (chloroform, c=1.858).

The employed starting material can be produced as follows:

24 g of ethyl-6-azido-6-deoxy-3,5-di-O-methyl-β-D-glucofuranoside is dissolved in 240 ml of methanol, and reduced, in the presence of 5% palladium/charcoal, with hydrogen. The catalyst is filtered off, and the filtrate is evaporated to dryness. The 6-amino derivative obtained is directly further reacted.

To a solution of 39.2 g of this product in 330 ml of ethanol is added dropwise within 40 minutes, with stirring, a solution of 10 ml of methylisocyanate in 30 ml of methylene chloride, and the reaction mixture is allowed to stand for 16 hours at room temperature. The reaction mixture is then evaporated to dryness, and the residue is taken up in ethyl acetate. This solution is filtered through active charcoal, and evaporated to dryness. The oil obtained is ethyl-6-deoxy-3,5-di-O-Methyl-6-(3-methylureido)-β-D-glucofuranoside with the $R_f$ value of 0.10 on silica gel in the system methylene chloride/methanol (15:1).

EXAMPLE 4

There are obtained in an analogous manner, commencing with the corresponding starting materials, the following compounds:
 (a) ethyl-2-O-acetyl-6-deoxy-3,5-di-O-methyl-6-(3-methyl-3-nitrosoureido)-D-glucofuranoside,
 (b) ethyl-6-(3-ethyl-3-nitrosoureido)-6-deoxy-3,5-di-O-methyl-D-glucofuranoside,
 (c) ethyl-6-[3-(2-chloroethyl)-3-nitrosoureido]-6-deoxy-3,5-di-O-methyl-D-glucofuranoside,
 (d) ethyl-6-(3-n-butyl-3-nitrosoureido)-6-deoxy-3,5-di-O-methyl-D-glucofuranoside,
 (e) ethyl-6-deoxy-5-O-methyl-6-(3-methyl-3-nitrosoureido)-3-O-propyl-D-glucofuranoside,
 (f) ethyl-5-O-ethyl-6-deoxy-6-(3-methyl-3-nitrosoureido)-3-O-propyl-D-glucofuranoside, and
 (g) ethyl-3-O-benzyl-6-deoxy-5-O-methyl-6-(3-methyl-3-nitrosoureido)-D-glucofuranoside.

EXAMPLE 5

A solution of 2.5 g of N-nitroso-methylcarbamylazide in 40 ml of ether is added dropwise in the course of 10 minutes, with stirring, to a solution, cooled to 0° C., of 5.0 g of ethyl-6-amino-6-deoxy-3,5-di-O-methyl-α-D-glucofuranoside in 40 ml of chloroform, and stirring is continued for a further 1 hour in an ice bath and for 3 hours at room temperature. The solution is then concentrated to a half, washed with ice-cold 2 N hydrochloric acid, with water, with a saturated sodium hydrogen carbonate solution and again with water, dried over magnesium sulphate and evaporated to dryness. The crystalline residue of ethyl-6-deoxy-3,5-di-O-methyl-6-deoxy-6-(3methyl-3-nitrosoureido)-α-D-glucofuranoside is recrystallised from ether/petroleum ether, m.p. 90°, $[\alpha]_D^{20} = +43° \pm 1°$ (chloroform, c=1.102).

EXAMPLE 6

A solution of 3.6 g of sodium nitrite in 20 ml of destillated water is added dropwise within 2 hours to a solution, cooled to 0° C., of 13.5 g ethyl-5-O-methyl-6-deoxy-6-(3-methylureido)-α-D-glucofuranoside in 150 ml of destillated water and 6.2 ml of glacial acetic acid. Stirring is maintained for 16 hours in an ice-bath, then the solution saturated with sodiumchloride and subsequently extracted 5 times with 200 ml of chloroform. The organic phases are combined, dried over sodium sulphate and evaporated to dryness. The residue is dissolved in 100 ml of destillated water and lyophilized to leave ethyl-5-O-methyl-6-desoxy-6-(3-methyl-3-nitrosoureido)-α-D-glucofuranoside melting at 54°–55° C., $[\alpha]_D^{20} = +65° \pm 1°$(Chloroform, C=1.003)

The starting material can be produced as follows: 8 g of sodiumhydride pract. (oilfree) is added to a solution of 52.6 g 6-azido-3-O-benzyl-6-deoxyl-1,2-O-isopropylidene α-D-glucofuranose in 600 ml N,N-dimethyl-formamide, the mixture is stirred for 1 hour at room temperature and then cooled at 0°. Then 19.2 ml methyliodide are added dropwise and the mixture stirred for another hour, then filtered and the filtrate evaporated to dryness. Destillated water is added to the residue and the whole extracted with either. The organic phase is washed with water till neutral, dried over magnesium sulphate and evaporated. The resulting 6-azido-3-O-benzyl-6-deoxyl-1,2-O-isopropylidene-5-O-methyl-α-D-glucofuranose is a yelloish oil. $[\alpha]_D^{20} = -59° \pm 1°$ (Chloroform, C=0.667).

A solution of 54.6 g of this compound in 430 ml of abs. ethanol and 120 ml of 4.6 N alcoholic hydrochloric acid is left to stand 18 hours at room temperature and then evaporated in a water-jet vacuum. The residue is taken up in ether and this solution is washed with a saturated sodium hydrogen carbonate solution and with distilled water, dried over magnesium sulphate and evaporated to dryness. By column chromatography on 1.2 kg of silica gel with methylene chloride/ethyl acetate (19/1) one obtains the ethyl-6-azido-3-O-benzyl-6-deoxy-5-O-methyl-α-D-glucofuranoside in the form of a colourless oil. $[\alpha]_D^{20} = +35° \pm 1°$ (Chloroform, C=0.834).

10.1 g of this compound in 100 ml ethanol are reduced in the presence of 0.5 g of 5% palladium/charcoal, with hydrogen for 90 minutes. The catalyst is filtered and 36.7 ml methylisocyanate is dropped, while stirring and cooling to the filtrate and the whole evaporated to dryness. The residue is crystallized from ethyl acetate/ether to obtain the ethyl-3-O-benzyl-6-deoxy-5-O-methyl-6-(3-methyl-ureido)-α-D-glucofuranosid. m.p. 92°-93,5°. $[\alpha]_D^{20} = +42° \pm 1°$ (Chloroform, C=0.973).

This product is dissolved in methanol and reduced and in the presence of 10% palladium/charcoal. There is thus obtained the ethyl-6-deoxy-5-O-methyl-6-(3-methylureido)-α-D-glucofuranoside as an oil. $[\alpha]_D^{20} = +73° \pm 1°$ (Chloroform, C=0.330).

EXAMPLE 7

A solution of 2.5 g N-Nitroso-methyl-carbamyl-azide in 40 ml of ether is added dropwise, while stirring, to a solution, cooled to 0°, of 4.7 g ethyl-6-amino-6-deoxy-5-O-methyl-α-D-glucofuranoside in 40 ml of chloroform. Stirring is maintained for 3 hours at room temperature. The solution is then evaporated to dryness and the residue dissolved in distilled water. This solution is extracted once with ether and the aqueous phase is lyophilized. There is thus obtained the ethyl-6-deoxy-5-O-methyl-6-(3-methyl-3-nitrosoureido)-α-D-glucofuranoside melting at 54°-55° C. $[\alpha]_D^{20} = +65° \pm 1°$ (Chloroform, C=0.914).

EXAMPLE 8

There are obtained in an analogous manner, commencing with the corresponding starting materials, the following compounds:

(a) ethyl-6-[3-(2-chloroethyl)-3-nitrosoureido]-6-deoxy-5-O-methyl-α-D-glucofuranoside
(b) ethyl-6-deoxy-6-(3-methyl-3-nitrosoureido)-α-D-glucofuranoside
(c) 6-deoxy-1,2-O-isopropylidene-6-(3-methyl-3-nitrosoureido)-α-D-glucofuranose
(d) 5-acetyl-6-deoxy-1,2-O-isopropylidene-6-(3-methyl-3-nitrosoureido)-α-D-glucofuranoside
(e) ethyl-5-O-ethyl-6-deoxy-6-(3-methyl-3-nitrosoureido)-α-D-glucofuranoside
(f) ethyl-6-deoxy-6-(3-methyl-3-nitrosoureido)-5-O-propyl-α-D-glucofuranoside
(g) ethyl-5-O-benzyl-6-deoxy-6-(3-methyl-3-nitrosoureido)-α-D-glucofuranoside
(h) methyl-6-deoxy-6-(3-methyl-3nitrosoureido)-5-O-methylα-D-glucofuranoside
(i) ethyl-6-deoxy-2,5-di-O-methyl-6-(3-methyl-3-nitrosoreido)-α-D-glucofuranoside
(k) ethyl-2-O-acetyl-6-deoxy-5-O-methyl-6-(3-methyl-3-nitrosoureido)-α-D-glucofuranoside
(l) 6-deoxy-1,2-di-O-acetyl-5-O-methyl-6-(3-methyl-3-nitrosoureido)-D-glucofuranoside
(m) benzyl-6-deoxy-5-O-methyl-6-(3-methyl-3-nitrosoureido)-D-glucofuranoside

I claim:

1. A $N_1$-Glucofuranosid-6-yl-$N_3$-nitroso-urea compound of the formula I

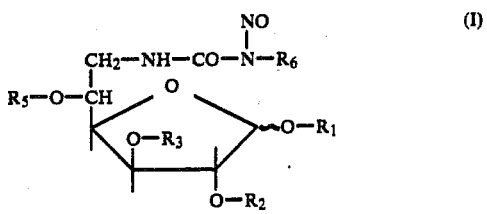

wherein anyone of $R_1$, $R_2$, $R_3$ and $R_5$ represent hydrogen, lower alkyl, lower alkyl substituted by hydroxy, lower alkoxy or halogen, phenyl-lower alkyl or naphthyl-lower alkyl, phenyl-lower alkyl or naphthyl-lower alkyl substituted in the phenyl or naphthyl moiety by lower alkyl, hydroxy, lower alkyl, lower alkylendioxy, halogen or trifluromethyl, an acyl residue of an organic carboxylic acid having 2 to 18 carbon atoms, a lower alkylsulphonic acid, a phenylsulphonic acid or a lower alkyl-phenylsulphonic acid, or $R_1$ and $R_2$ together or $R_3$ and $R_5$ together represent also a lower alkylidene or a cycloalkylidene having 5 to 6 carbon atoms, and $R_6$ represents lower alkyl or lower alkyl substituted by hydroxy, lower alkoxy or halogen.

2. A compound as claimed in claim 1 wherein $R_1$ and $R_2$ each represent hydrogen, lower alkyl, lower alkyl substituted by hydroxyl, lower alkoxy or halogen, benzyl, benzyl substituted by hydroxyl, lower alkoxy, halogen or trifluoromethyl, or $R_1$ and $R_2$ together also represent lower alkylidene or cycloalkylidene having 5-6 carbon atoms, $R_3$ and $R_5$ each represent hydrogen, lower alkyl, lower alkyl substituted by hydroxyl, lower alkoxy or halogen, benzyl, benzyl substituted by hydroxyl, lower alkoxy, halogen or trifluoromethyl, lower alkanoyl, benzoyl or benzoyl substituted by halogen, lower alkoxy, hydroxyl or lower alkanoyloxy, or $R_3$ and $R_5$ together also represent lower alkylidene or cycloalkylidene having 5-6 carbon atoms, and $R_6$ represents lower alkyl, lower alkyl substituted by halogen, hydroxyl or lower alkoxy.

3. A compound as claimed in claim 1 wherein $R_1$ represents lower alkyl, and $R_2$ represents hydrogen, or $R_1$ and $R_2$ together represent lower alkylidene, $R_3$ and $R_5$ each represent hydrogen, lower alkyl, benzyl, benzyl substituted by halogen, hydroxyl, lower alkoxy or alkyl, and $R_6$ represents lower alkyl or lower alkyl substituted by chlorine.

4. Compounds according to claim 2, wherein the substituted benzyl group is substituted in the para-position.

5. Compounds as claimed in claim 1 of the formula I, wherein $R_1$ represents hydrogen, methyl, ethyl or propyl, and $R_2$ represents hydrogen, and $R_1$ and $R_2$ together represent the isopropylidene group, and $R_3$ and $R_5$ represent methyl, and $R_6$ represents methyl or chloroethyl.

6. Compounds as claimed in claim 1 of the formula I, wherein $R_1$ represents hydrogen, methyl, ethyl or propyl, $R_2$ and $R_3$ represent hydrogen, and $R_1$ and $R_2$ together represent the isopropylidene group and $R_5$ represents methyl and $R_6$ represents methyl or chloroethyl.

7. The α- or β-anomers of the compounds as claimed in claim 1.

8. The compounds as claimed in claim 1 having the formula I, wherein $R_1$ and $R_2$ together represent isopropylidene or, $R_1$ is ethyl and $R_2$ is acetyl and each of $R_3$, $R_5$ and $R_6$ is methyl.

9. The compounds as claimed in claim 1 having the formula I wherein $R_1$ is ethyl, $R_2$ is hydrogen, $R_3$ and $R_5$ each is methyl and $R_6$ is ethyl, chloroethyl or n-butyl.

10. The compound as claimed in claim 1, having the formula I wherein $R_1$ is ethyl, $R_2$ is hydrogen, $R_3$ is hydrogen, n-propyl or benzyl, $R_5$ is methyl or ethyl and $R_6$ is methyl.

11. The compound as claimed in claim 1, having the formula I, wherein $R_1$ is ethyl, $R_2$ is hydrogen $R_3$, $R_5$ and $R_6$ are methyl.

12. The compound as claimed in claim 1, having the formula I, wherein $R_1$ is ethyl, $R_2$ and $R_3$ are hydrogen and $R_5$ and $R_6$ are methyl.

13. A pharmaceutical preparation useful for inhibition of tumors of Ehrlich's ascitic carcinoma or solid Harding - Passey's melanoma or Yoshida's ascitic sarcoma, or leukaemia L 1210 or Rauscher's leukaemia in mice and rats, which comprises a therapeutically effective amount of a compound claimed in claim 1 and a pharmaceutically acceptable carrier thereof.

14. A method of inhibiting tumors of Ehrlich's ascitic carcinoma, solid Harding-Passey's melanoma or Yoshida's ascitic sarcoma, or leukaemia L 1210 or Rauscher's leukaemia in mice and rats, comprising administering to said animals a therapeutically effective amount of a compound of claim 1.

* * * * *